(12) United States Patent
Vollrath

(10) Patent No.: US 7,041,797 B2
(45) Date of Patent: May 9, 2006

(54) PRECURSOR SILK FEEDSTOCK FOR FORMING FILAMENTS

(75) Inventor: Fritz Vollrath, Berkley (GB)

(73) Assignee: Spin'Tec Engineering GmbH, Fellbach (DE)

( * ) Notice: Subject to any disclaimer, the term of this patent is extended or adjusted under 35 U.S.C. 154(b) by 0 days.

(21) Appl. No.: 10/494,349

(22) PCT Filed: Oct. 28, 2002

(86) PCT No.: PCT/EP02/12033

§ 371 (c)(1),
(2), (4) Date: Jul. 19, 2004

(87) PCT Pub. No.: WO03/037925

PCT Pub. Date: May 8, 2003

(65) Prior Publication Data

US 2005/0065323 A1 Mar. 24, 2005

(30) Foreign Application Priority Data

Oct. 31, 2001 (GB) .................................... 0126118

(51) Int. Cl.
*A61K 38/17* (2006.01)
(52) U.S. Cl. ..................................... 530/353
(58) Field of Classification Search ................ 424/401; 514/21; 435/391
See application file for complete search history.

(56) References Cited

FOREIGN PATENT DOCUMENTS

| CN | 1092284 | 9/1994 |
|---|---|---|
| EP | 0 352 330 | 1/1990 |
| EP | 1 004 699 | 5/2000 |
| EP | 1 241 178 | 9/2002 |
| JP | 48-15960 | 5/1973 |
| JP | 220068693 | 11/1990 |
| JP | 320009399 | 9/1991 |
| JP | 610084809 | 7/1994 |
| JP | 090019238 | 1/1997 |
| JP | 090070241 | 3/1997 |
| WO | WO 01/38614 | 5/2001 |

OTHER PUBLICATIONS

Ochi, A., et al. 2002. Biomacromolecules 3: 1187-1196.*
Kenney, J.M., et al. 2002. Eur. J. Biochem. 269: 4159-4163.*
Inoue, S., et al. 2000. J. Biol. Chem. 275(51): 40517-40528.*
"Liquid crystals and flow elongation in a spider's silk production line." Proceedings of the Royal Society of London, Series B, (Mar., 1999), vol. 266, No. 1418, pp. 519-523. (ab).
"Silk Production in a spider involves acid bath treatment." Proceedings of the Royal Society of London, Series B, Biological Sciences, (May 1998), vol. 265, No. 1398, pp. 817-820. (ab).
"Reduced Level of Secretion and Absense of Subunit Combination for the Fibroin Synthesized by a Mutant Silkworm, Nd(2)," *The Journal of Cell Biology*, vol. 99, Pgs. 2005-2010, Dec. 1984.

* cited by examiner

*Primary Examiner*—Karen Cochrane Carlson
*Assistant Examiner*—Marsha Tsay
(74) *Attorney, Agent, or Firm*—Steven J. Hultquist; Intellectual Property/Technology Law

(57) ABSTRACT

The application relates to a method of obtaining silk feedstock solution from a gland of a silkworm or another silk-producing arthropod in which the body of the silkworm or the other silk-producing arthropod is cut open and the gland removed. The silk feedstock solution is subsequently extracted from the gland and used for extrusion, spinning or moulding of objects.

14 Claims, No Drawings

PRECURSOR SILK FEEDSTOCK FOR FORMING FILAMENTS

CROSS-REFERENCE TO RELATED APPLICATIONS

This application is filed under the provisions of 35 USC §371 based on International application no. PCT/EP02/12033 filed Oct. 28, 2002, claiming the priority of Great Britain application 0126118.9 filed Oct. 31, 2001. The priority of such applications is hereby expressly claimed.

FIELD OF THE INVENTION

This invention relates to feedstock material for spinning of proteinaceous fibres.

PRIOR ART

There is currently much interest in apparatus and processes that enable the manufacture of polymer filaments. Strong, tough filaments are useful for the manufacture, by way of example only, of threads, cords, ropes, ribbons and wound, woven or fleece materials. Filaments can also be incorporated into a matrix with or without other filler particles to produce tough and resilient composite materials. Natural silks are fine, lustrous threads produced by the silkworm, *Bombyx mori*, and other insect or arachnid species. Such silks offer distinct advantages when compared with many synthetic polymers currently used for the manufacture of filaments. The tensile strength and toughness of some silks can equal or even exceed that of Kevlar™, one of the strongest of man-made fibres. Silks such as spider dragline also show exceptional thermal stability. Many silks are also biodegradable and do not persist in the environment. They are recyclable and are produced by a highly efficient low pressure and low temperature process using only water as a solvent. The natural spinning process is remarkable in that an aqueous solution of protein is converted into a tough and highly insoluble filament. There are a number of methods both conventional or biomimetic to spin fibres from protein feedstock in order to make fibres. All of these methods rely on synthesized or genetically modified precursor peptide, protein or protein/synthetic feedstock.

Natural silk is derived commercially from the silkworm which spins a cocoon that is then heated and chemically treated to allow its filaments to soften and unglue making it possible to unravel the cocoon and wind the resulting filament onto a bobbin from which they can then be twisted into threads. The commercial silk industry has a history of many thousand years during which silk worms (*Bombyx mori*) and other lepidopteran species have been bred to produce many races with silks of different qualities. Recently *Bombyx* silk worms have also been genetically modified to give an even wider range of silks. In all cases, however, the spinning of the feedstock is left to the insect itself and thus spinning occurs 'in vivo'.

There are many published and known processes and methods to produce silk-like materials or materials derived from silk using not only synthetic feedstock but also recombinant feedstock made from silk sequences expressed for example in bacterial yeast, vascular plants or even goat milk. It has been suggested that such materials are likely to have highly useful properties. It has also been suggested that the performance of such materials is likely to be improved by matching the extrusion or moulding technology with the properties of the feedstock or vice versa. It will be appreciated that the feedstock solutions required for the manufacture of fibres must have specific properties. There are many patents relating to such feedstock, such as U.S. Pat. No. 5,728,810, U.S. Pat. No. 5,756,677, U.S. Pat. No. 6,268,169 and U.S. Pat. No. 6,184,348, which discuss the preparation of synthetic silk protein polymers either by genetic (recombinant) or chemical modification.

There are other inventions discussing the extraction of particular ingredients such as sericin from silk and silk glands for use for example in healthcare and beauty creams.

An example of such an invention is disclosed in Chinese patent application Nr. CN-A-1092284 in which a silkworm is cut into fine pieces prior to being soaked in water. According to this patent application, multiple kinds of amino acids are extracted from the silkworm which can be used to make a skin protection product.

Prior art disclosing methods of extracting feedstock from silkworms include Japanese Patent Application No. JP-A-6-184809 (Saito) in which the larvae in the final instar are pressed to death in order to extract the feedstock from their silk glands. Using this method, however, the feedstock is contaminated with body fluids of the silk worm. The removal of these body fluids requires an additional purification step to produce feedstock for spinning or other extrusion methods. Even after purification, some impurities from the body fluids may remain in the feedstock to cause contamination that affects the properties of the final spun material. Moreover, such purifications require addition chemical treatments that in all likelihood seriously degrade the original feedstock.

Japanese patent application No. JP-A-2-686693 (Asahi Chemical) describes a method by which silk fibroin is apparently cultivated using rear silk glands in a culture medium.

Similarly, Japanese patent application Nr. JP-A-3-209399 (Terumo Corp) teaches a method in which the heads are cut off the silkworms and their abdomina squeezed in order to obtain the silk protein. Again, this method suffers from the disadvantage that not only are silk proteins obtained, but also impurities from the body fluids which requires potentially detrimental chemical removal of the fibroins.

Methods for cutting open the silkworm to extract useful materials from the silk worm are described, for example, in Japanese Patent Application Nr. 9-019238 (Toray Industries). This publication discloses an ultrasonic cutter which cuts open the silk worm in order to extract the body fluids, such as interferon. A further method is disclosed in Japanese patent application JP-A-9-070241 (Toray) in which a rotating blade is used to cut open the silkworm.

SUMMARY OF THE INVENTION

An object of the present invention is to provide raw silk feedstock material for use in subsequent forming operations by extracting the feedstock material directly from silk glands of silkworms or other silk-producing arthropods. By cutting open the body of the silkworm and removing the gland, followed by extracting the silk feedstock solution, contamination of the silk feedstock solution by other body fluids is substantially reduced or prevented totally. This means that the silk feedstock solution does not need to be purified prior to use in, for example, spinning or extrusion. It is believed that the best raw silk feedstock material is one that is substantially free from impurities and moreover is little chemically modified from the original feedstock material directly extracted from the glands of the silkworms or other silk-producing arthropods.

The silk feedstock solution can further be advantageously placed in dissolved water for a period of time in order to remove sericin protein in the silk feedstock solution. This leaves a silk feedstock solution that comprises substantially fibroin protein.

In a further embodiment of the invention, the silk feedstock solution is treated with a cross-linking agent, such as an aldehyde. The cross-linking agent introduces covalent bonds between and probably within the protein chains to enhance the mechanical properties of spun or extruded material as well as material formed or poured into shapes as required. One example of this use is in the preparation of a filler, such as for insertion in a bone cavity prepared for an implant such as an artificial hip. After insertion of the peg of the hip, the filler is crosslinked form a firm and perfectly shaped grip linking bone and the implant.

DETAILED DESCRIPTION OF THE INVENTION

The present invention refers to the direct removal of silk precursor solution directly from the glands of silkworms or other silk producing arthropods. The glands of the silkworm comprise an epithelial layer of tissue consisting largely of a layer of columnar cells surrounded by a basement membrane of structural proteins. Inside the epithelium is a coating of sericin made up of five or so different sericin layers. The coating of sericin surrounds a thick core of fibroin.

The precursor solution may be collected and stored and be subjected, if desired, to chemical or physical modification for use as a feedstock for extrusion into filaments or for moulding the material while it sets to produce objects with desired shape. This has the advantage of reducing the labour cost involved in unwinding of cocoons and is likely to produce materials with superior properties. An additional advantage is that, unlike the natural spinning process that is extremely difficult to control, the present approach enables rigorous control of the extrusion or moulding process so that the properties of the resulting materials can, in theory, be tuned to the desired end use. By way of example only, the feedstock material of the present invention can be used in methods of forming materials as disclosed in WO 01/38614, the disclosure of which is incorporated in this application. It appears important that for best effect the spinning solution taken from a silkworm is as free from impurities as possible, and also as little chemically modified from the original raw silk solution as possible.

The invention thus relates to the preparation of silk feedstock solutions by removing aqueous solutions of silk protein directly from the silk glands of silkworms as a precursor from which to extrude or mould materials. It will be appreciated that such raw silk feedstock material can be obtained directly from the silk glands either by dissection or by extraction with a suitable solvent or solvent system as described in more detail hereinafter. The feedstock may be extracted towards the end the final larval instar in order to get a maximum amount the fibroin protein and a minimum amount of the sericin protein. However, the feedstock might be extracted at other larval instarts or during other time periods during the final larval instar. The extracted silk protein solutions can be diluted, concentrated, chemically or physically modified, handled and stored in readiness for extrusion or moulding.

The extracted silk protein solutions comprise both sericin and fibroin proteins. The *Bombyx* more fibroin dope can be regarded as a mixture of three proteins the ratio of five molecules of fibroin heavy chain, 5 molecules of fibroin light chain and 1 molecule hexamerin (=P25). It is believed that the hexamerin holds the hexamers formed from the other two units together, hence the 5.5.1 ratio. It is very likely that these have to be assembled into 5.5.1 hexameric units for optimum results.

The fibrioin heavy chain protein has been sequenced and deposited under the accession number FBOH_BOMMO (P05790) Fibroin heavy chain precursor (Fib-H) (H-fibroin). It is encoded by the gene FIBH-*Bombyx mori* (Silk moth). Sequencing is described in the article by Zhou C.-Z., Confalonieri F., Medina N., Zivanovic Y., Esnault C., Yang T., Jacquet M., Janin J., Duguet M., Perasso R., Li Z.-G. "Fine organization of *Bombyx mori* fibroin heavy chain gene.", pulished in Nucleic Acids Res. 28:2413–2419(2000).

The fibroin light chain protein has been sequenced and deposited under the accession number FBOL_BOMMO (P21828) Fibroin light chain precursor (Fib-L) (L-fibroin). It is encoded by the gene FIBL-*Bombyx mori* (Silk moth). Sequencing is described in the article by Yamaguchi K., Kikuchi Y., Takagi T., Kikuchi A., Oyama F., Shimura K., Mizuno S. "Primary structure of the silk fibroin light chain determined by cDNA Sequencing and peptide analysis." Published in J. Mol. Biol. 210:127–139(1989). The sequencing is additionally described in Kikuchi Y., Mori K., Suzuki S., Yamaguchi K., Mizuno S., "Structure of the *Bombyx mori* fibroin light-chain-encoding gene: upstream sequence elements common to the light and heavy chain", published in Gene 110:151–158(1992).

A variety of extrusion and moulding techniques can be used to form the final materials as is commonly known to a craftsman skilled in the art. Specific examples of further treating steps are given in more detail hereinafter.

According to another aspect of the present invention there is provided the use of silk precursor solutions taken from the glands of silkworms or other silk producing arthropods as feedstock from which to extrude or mould filaments or other structures.

In particular the glands may be taken from silkworm larvae and other lepidoptera or arachnida. The extracted material can be extruded into high quality fibres using existing spinning or moulding technologies.

By way of example only there follows a method according to which the protein solution can be extracted. In this method the glands are removed by dissection and the concentrated spinning solution in them is retained with or without removal of the epithelial layer by dissection. The glands are removed by slicing open the body of the silkworm or other silk-producing arthropods. The preferred method uses removal of the epithelial layer after a brief treatment in distilled water. Alternatively, other solvents could be used. The resulting concentrated protein can be pooled with other protein extracted in this way and stored, preferably at 4° C., before use. Protease inhibitors may be added to prevent degradation of the protein during storage as known by persons skilled in the art. A treatment with water or aqueous solution to remove sericin or other easily soluble compounds may be instituted before or after pooling the glands. The concentrated protein solution is preferably stored in a siliconized container to prevent degradation during storage and preferably under silicone oil. The concentrated protein solution can be used directly or can be diluted with water or other solutions or solvents before use. It can be further treated or used directly. Prolonged storage is possible after freeze drying the spinning solution before or after dilution.

Examples of further treatment steps after extraction of the protein solution involve treatment with aqueous or non-aqueous solutions or buffers or treatment with vapour from volatile acids or bases or volatile buffers. A further example is the addition of mono or divalent ions to condition the spinning solution. These conditioning solutions can be achieved to the spinning solution through a semipermeable or porous membrane as described, for example, in WO 01/38614.

The solution may be treated by the addition of an aldehyde solution such as glutaraldehyde to cross-link the constituents of the spinning solution. Other aldehydes or cross-linking agents could be used as will be understood by persons skilled in the art. Other conditioning agents can be added to the spinning solution.

The final processing of the spinning solution can be achieved in a variety of ways. These include conventional solution or gel spinning techniques; spinning through dies with one or more semipermeable or porous regions; moulding; blow moulding; and blown extrusion. In one embodiment the solution may be allowed to flow into a mould. The solution is then treated with an aldehyde or other cross-linking agent in solution or as vapour applied directly or through a semipermeable membrane forming substantially all or part of the walls of the mould. A similar aldehyde can be applied immediately before the spinning solution enters a blow moulding mould or an annular die used for blown extrusion.

EXAMPLES

Two illustrative examples of the invention will now be described. These examples are not intended to be limiting of the invention.

Example 1

A final instar of the silkworm, Bombyx mori, is selected. The instar was approximately 7 cm long and contained a gland having several milligrams of protein mixture. The protein dope contained fibroin and sericin. The gland was removed by dissecting the silkworm. Care was taken to avoid substantial contamination with the silkworm's bodily fluids. The gland was then immersed in distilled water for two minutes.

The epithelium of the gland was removed by knife and the protein dope mixture extracted from the gland. The protein mixture was fixed in a 2% glutaraldehyde solution in a 0.1 M phosphate buffer, having a pH of 7.4 for twelve hours. The resulting cross-linked mixture appeared to have good mechanical properties.

Example 2

The glands were removed as described above and the epithelium removed. The protein mixture placed into distilled water and agitated for around 30 minutes. The sericin protein dissolved into the distilled water to leave substantially fibroin protein in the protein mixture. The fibroin protein was blotted dry and placed into a mould for storage.

The invention claimed is:

1. A method of obtaining silk feedstock solution from a gland of a silkworm or another silk-producing arthropod, wherein the gland has an epithelial layer, comprising:
   a first step of cutting open a body of the silkworm or the other silk-producing arthropod;
   a second step of removing the gland from the body;
   a third step of removing the epithelial layer; and
   a fourth step of extracting the silk feedstock solution from the gland.

2. The method according to claim 1, wherein the epithelial layer is removed by dissection prior to extracting the silk feedstock solution.

3. The method according to claim 2, comprising treatment of the gland with a solvent prior to removal of the epithelial layer.

4. A method of obtaining silk feedstock solution from a gland of a silkworm or another silk-producing arthropod, comprising: a first step of cutting open a body of the silkworm or other silk-producing arthropod; a second step of removing the gland; and a third step of extracting the silk feedstock solution from the gland, in which the silk feedstock solution is treated with a cross-linking agent.

5. The method of claim 4 wherein the cross-linking agent is an aldehyde.

6. A silk feedstock solution in pure and isolated form, as directly isolated from a gland of a silkworm or other silk-producing arthropod, wherein the gland has an epithelial layer, by:
   a first step of cutting open a body of the silkworm or the other silk-producing arthropod;
   a second step of removing the gland from the body;
   a third step of removing the epithelial layer; and
   a fourth step of extracting the silk feedstock solution from the gland.

7. The silk feedstock solution of claim 6 being substantially made of fibroin protein.

8. A method of making an extruded or molded object, comprising use of the silk feedstock solution of claim 6 as feedstock in extrusion or molding of said object.

9. A silk feedstock solution obtained from a silkworm or another silk-producing arthropod using the method of claim 2.

10. A silk feedstock solution obtained from a silkworm or another silk-producing arthropod using the method of claim 3.

11. A silk feedstock solution obtained from a silkworm or another silk-producing arthropod using the method of claim 4.

12. A silk feedstock solution obtained from a silkworm or another silk-producing arthropod using the method of claim 5.

13. The method according to claim 3, wherein said solvent comprises water.

14. The method according to claim 3, wherein said solvent comprises distilled water.

* * * * *

UNITED STATES PATENT AND TRADEMARK OFFICE
CERTIFICATE OF CORRECTION

PATENT NO. : 7,041,797 B2  Page 1 of 1
APPLICATION NO. : 10/494349
DATED : May 9, 2006
INVENTOR(S) : Fritz Vollrath It is certified that error appears in the above-identified patent and that said Letters Patent is hereby corrected as shown below:

In Column 1, Line 62, "bacterial yeast" should be -- bacteria, yeast --.

Signed and Sealed this

Eighth Day of August, 2006

JON W. DUDAS
*Director of the United States Patent and Trademark Office*